United States Patent [19]

Potts

[11] 3,966,926

[45] June 29, 1976

[54] COMPOSITION OF A STEROIDAL[2,3-d]-ISOXAZOLE AND METHOD OF USE THEREOF

[75] Inventor: Gordon O. Potts, Chatham, N.Y.

[73] Assignee: Sterling Drug Inc., New York, N.Y.

[22] Filed: Mar. 26, 1975

[21] Appl. No.: 562,122

[52] U.S. Cl. .................. 424/241; 260/239.55 R
[51] Int. Cl.² ................................ A61K 31/58
[58] Field of Search ............. 424/241; 260/239.55

[56] References Cited
UNITED STATES PATENTS 3,135,743  6/1964  Clinton et al. ............. 260/239.55

*Primary Examiner*—Ethel G. Love
*Attorney, Agent, or Firm*—Thomas L. Johnson; B. Woodrow Wyatt

[57] ABSTRACT

The compound 17β-hydroxy-4,4,17α-trimethylandrost-5-eno[2,3-d]isoxazole and its esters are useful in disrupting pregnancy in female mammals upon oral administration.

2 Claims, No Drawings

COMPOSITION OF A STEROIDAL[2,3-D]-ISOXAZOLE AND METHOD OF USE THEREOF

BACKGROUND OF THE INVENTION

1. Field of the Invention

This invention relates to a novel composition comprising a steroid having abortifacient activity and a method for disrupting pregnancy therewith.

2. Description of the Prior Art

A class of chemical compounds known as steroido[2,3-d]isoxazoles is described in Clinton et al. U.S. Pat. No. 3,135,743. The compounds are there stated to have useful metabolic, hormonal and anti-hormonal properties, in particular, one or more of the following activities: anabolic, androgenic, pituitary inhibiting, estrogenic, progestational and adrenal cortical.

A specific compound disclosed in Example 22 of U.S. Pat. No. 3,135,743 is 17β-hydroxy-4,4,17α-trimethylandrost-5-eno[2,3-d]isoxazole having the formula

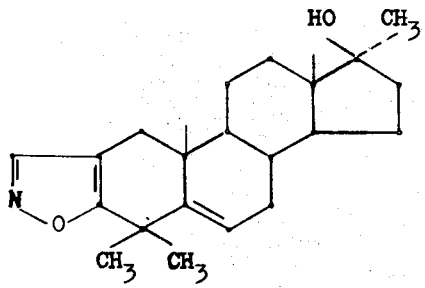

I

Compound I is stated in the patent to process a blocking action on the adrenal response to ACTH in castrated male rats.

SUMMARY OF THE INVENTION

In a composition of matter aspect, the invention relates to a composition for disrupting pregnancy in a female mammal which comprises an abortifaciently effective amount of 17β-hydroxy-4,4,17α-trimethylandrost-5-eno[2,3-d]isoxazole or a pharmaceutically acceptable ester thereof incorporated in an inert pharmaceutical carrier.

In a process aspect, the invention relates to a method for disrupting pregnancy in a female mammal which comprises administering orally to said mammal, subsequent to implantation of a fertilized ovum in said mammal, an abortifaciently effective amount of 17β-hydroxy-4,4,17α-trimethylandrost-5-eno[2,3-d]isoxazole or a pharmaceutically acceptable ester thereof.

DETAILED DESCRIPTION INCLUSIVE OF PREFERRED EMBODIMENTS

17β-Hydroxy-4,4,17α-trimethylandrost-5-eno[2,3-d]isoxazole (Compound I) blocks the conversion of pregnenolone to progesterone, and thus inhibits the formation of ovarian or placental progesterone necessary for the maintenance of pregnancy. Compound I is thus effective as an abortifacient at a time immediately after implantation of the fertilized ovum and at any time during the pregnancy while progesterone is essential for maintenance of the pregnancy.

In the method aspect of the invention Compound I or ester thereof is preferably administered in a daily dose of between 25 and 100 mg/kg of body weight for a period of between one and five days; and preferably at a time at least about 8 days after exposure to insemination.

When Compound I was administered intragastrically in a 10% ethanol-oil vehicle to female rats 10 days after insemination, the following results were obtained:

| Group | Test Agent | Dose mg/kg/day × 1 | No. of Rats | No. Pregnant | Pregnancy Rate (%) |
|---|---|---|---|---|---|
| 1 | Vehicle | — | 7 | 6 | 86 |
| 2 | Compound I | 6.0 | 7 | 5 | 71 |
| 3 | Compound I | 12.0 | 7 | 3 | 43 |
| 4 | Compound I | 24.0 | 7 | 5 | 71 |

| Group | Body Weight Initial | Body Weight Final | Observations: Implantation Sites | Av.Nos./Preg. Resorption Sites | Rat Fetuses | Fetal Viability (%) |
|---|---|---|---|---|---|---|
| 1 | 246 | 282 | 13.1 | 0.8 | 12.3 | 100 |
| 2 | 247 | 294 | 12.8 | 5.6 | 7.2 | 100 |
| 3 | 247 | 272 | 13.0 | 13.0 | 0 | 0 |
| 4 | 246 | 271 | 13.4 | 13.4 | 0 | 0 |

The data of the foregoing table showed that Compound I was active as an abortifacient agent. It was partially effective at a dose level of 6 mg/kg and completely effective at 12 and 24 mg/kg.

Compound I was tested for oral abortifacient activity in the rhesus monkey (*Macaca mulatta*) according to the following experiments:

Experiment I

Female monkeys with regular menstrual cycles were mated on days 11–16 of the menstrual cycle. Beginning on day 24 of the cycle and daily for 5 days, the monkeys were medicated by stomach tube with Compound I at a dose of 1000 mg per monkey per day or 20 ml of the 10 percent ethanol in cottonseed oil vehicle. Blood was obtained by femoral puncture approximately 21 days after the middle of the mating period and was bioassayed for chorionic gonadotrophin. The matings and medications were repeated for up to 9 consecutive menstrual cycles.

| | No. of Monkeys | No. of Treatment Cycles | No. of Monkeys Pregnant |
|---|---|---|---|
| 20 ml Alc-oil per monkey per day × 5 i.g. | 8 | 33 | 8 |
| Compund I, 1000 mg per | | | |

| | No. of Monkeys | No. of Treatment Cycles | No. of Monkeys Pregnant |
|---|---|---|---|
| monkey per day × 5 i.g. | 10 | 52 | 0 |

The above results showed that none of the ten monkeys treated with Compound I were pregnant during 52 menstrual cycles while all eight of the vehicle treated control animals were pregnant during 33 cycles.

Experiment II

Pregnant monkeys were medicated with Compound I at doses of 100 or 1000 mg per monkey per day for 5 days or 20 ml of the 1 percent gum tragacanth vehicle. Pregnancy was determined by the presence of chorionic gonadotrophin in serum obtained 21–26 days after conception. The serum was bioassayed and the monkeys were estimated to be from 24–35 days pregnant when treatment was initiated. Monkey chorionic gonadotrophin is not uniformly detectable after day 26 of pregnancy and therefore the status of the pregnancy was determined by rectal palpation of the uterus and the presence or absence of vaginal bleeding.

| Treatment | No. of Monkeys | No. of Monkeys that aborted | No. of Monkeys that resumed Menstrual Cycles |
|---|---|---|---|
| 20 ml 1% Gum Tragacanth × 5 i.g. | 7 | 0 | 0 |
| Compound I - 100 mg per monkey per day × 5 i.g. | 5 | 0 | 0 |
| Compound I - 1000 mg per monkey per day × 5 i.g. | 6 | 6 | 5 |

This experiment showed that administration of Compound I at a dose of 1000 mg per monkey per day for five days uniformly terminated pregnancy in monkeys 24–35 days after conception.

Experiment III

Pregnant monkeys were medicated for 5 days with Compound I at a dose of 1000 mg per monkey per day administered in 1 percent gum tragacanth at the end of the first trimester of pregnancy, that is when the monkeys were approximately 50 days pregnant. The condition of the pregnancy was determined by rectal palpation, the presence or absence of vaginal bleeding, or the observation of an aborted fetus. Compound I was prepared for administration as a solution/suspension in a 10 percent ethanol in cottonseed oil vehicle or in 1 percent gum tragacanth. Rapid and complete abortion occurred in four monkeys.

Termination of pregnancy by administration of Compound I has been observed in monkeys as much as 80 days pregnant.

Compound I can also be used in the form of a pharmaceutically acceptable ester thereof wherein the 17-hydroxy group is esterified with a carboxylic acid. The carboxylic acid moiety preferably has from one to about ten carbon atoms and a molecular weight less than about 200, of the types described in U.S. Pat. No. 3,135,743. The esters are prepared by conventional esterification procedures, as illustrated by the following examples.

EXAMPLE 1

17β-Hydroxy-4,4,17α-trimethylandrost-5-eno[2,3-d]isoxazole formate

A mixture of 40.8 ml. of acetic anhydride and 17.2 ml. of formic acid was heated for 2 hours at 50°–60°C. There was then added 17.78 g. of 17β-hydroxy-4,4,17α-trimethylandrost-5-eno[2,3-d]isoxazole and the mixture stirred for 2 hours at 55°C. and 1 hour at 65°C. The reaction mixture was quenched in ice-water, filtered, and the solid product washed with water and dried at 65°C. to give 17.34 g., m.p. 188°–196°C. The latter was recrystallized twice from acetonitrile to give 8.66 g. of 17β-hydroxy-4,4,17α-trimethylandrost-5-eno[2,3-d]isoxazole formate, m.p. 200°–202°C. (uncorr.), $[\alpha]_D^{25} = -50.0°$ (1% in chloroform). This formate ester was found to be completely effective as an abortifacient agent when administered intragastically to female rats 10 days after insemination at a dose level of 12.0 mg/kg/day × 1.

EXAMPLE 2

17β-Hydroxy-4,4,17α-trimethylandrost-5-eno[2,3-d]isoxazole cyclohexanepropionate A mixture of 10 g. of 17β-hydroxy-4,4,17α-trimethylandrost-5-eno[2,3-d]isoxazole, 41.2 g. of cyclohexanepropionic anhydride and 60 ml. of pyridine was heated at reflux for 7 hours. The reaction mixture was poured into water, the water decanted from the oily product and the latter dissolved in ether. The ether solution was washed with water, dried, and the solvent removed. The residual mobile oil (37.7 g.) was dissolved in pentane and chromatographed on 500 g. of silicon dioxide. The chromatogram was eluted with pentane and with pentane containing increasing amounts of ether. Eluants from pentane containing 5–10% ether brought out the desired product (about 8 g.) which was recrystallized from methanol to give 17β-hydroxy-4,4,17α-trimethylandrost-5-eno[2,3-d]isoxazole cyclohexanepropionate, m.p. 117°–121.5°C. (corr.), $[\alpha]_D^{25} = -32.2°$ (1% in chloroform).

The composition aspect of the invention comprises an abortifaciently effective amount of 17β-hydroxy-4,4,17α-trimethylandrost-5-eno[2,3-d]isoxazole or a pharmaceutically acceptable ester thereof incorporated in an inert pharmaceutical carrier. Said composition is prepared by dissolving or suspending it in a pharmaceutically acceptable liquid vehicle, e.g. aqueous alcohol, glycol, cottonseed oil solution or oil-water emulsion, gum tragacanth suspension, or the like; or by incorporating it in unit dosage form as tablets or capsules either alone or in combination with conventional adjuvants, e.g. calcium carbonate, starch, lactose, talc, magnesium stearate, gum acacia, and the like. Illustrative capsule mix formulations are as follows:

| | mg/capsule | mg/capsule |
|---|---|---|
| Compound I* (micronized) | 100 | 200 |
| Starch | 62 | 76.6 |
| Lactose | 62 | 76.6 |
| Talc | 5 | 5 |
| Magnesium stearate | 1 | 1.8 |

|  | mg/capsule | mg/capsule |
|---|---|---|
| Net Weight | 230 | 360 |

*17β-hydroxy-4,4,17α-trimethylandrost-5-eno[2,3-d]isoxazole

I claim:

1. A method for disrupting pregnancy in a female mammal which comprises administering orally to said mammal, subsequent to implantation of a fertilized ovum in said mammal, an abortifaciently effective amount of 17β-hydroxy-4,4,17α-trimethylandrost-5-eno[2,3-d]isoxazole or a pharmaceutically acceptable ester thereof.

2. A method according to claim 1 in which 17β-hydroxy-4,4,17α-trimethylandrost-5-eno[2,3-d]isoxazole is administered in a daily dose of between 25 and 100 mg/kg of body weight for a period of between 1 and 5 days.

* * * * *